US006376185B1

(12) United States Patent
Malinka et al.

(10) Patent No.: US 6,376,185 B1
(45) Date of Patent: Apr. 23, 2002

(54) **DNA SEQUENCES OF GENES FROM *FIMBRIAE D'ESCHERICHIA COLI* STRAIN DSM 6601**

(75) Inventors: Jürgen Malinka, Selm; Jörg Hacker, Gerbrunn; Gabriele Blum-Oehler, Würzburg; Ulrich Sonnenborn, Bochum; Jürgen Schulze, Bergholz-Rehbrücke; Hans Proppert, Hagen, all of (DE)

(73) Assignee: Pharma-Zentrale GmbH (DE)

( * ) Notice: Subject to any disclaimer, the term of this patent is extended or adjusted under 35 U.S.C. 154(b) by 0 days.

(21) Appl. No.: 09/554,834

(22) PCT Filed: Nov. 18, 1998

(86) PCT No.: PCT/EP98/07397

§ 371 Date: Jul. 13, 2000

§ 102(e) Date: Jul. 13, 2000

(87) PCT Pub. No.: WO99/25869

PCT Pub. Date: May 27, 1999

(30) Foreign Application Priority Data

Nov. 19, 1997 (DE) .......................................... 197 51 242

(51) Int. Cl.$^7$ ................................................. C12Q 1/68
(52) U.S. Cl. .................... 435/6; 435/91.1; 435/91.2; 435/252.1; 424/93.1
(58) Field of Search ..................... 435/6, 91.1, 91.2, 435/252.1; 424/93.1

(56) References Cited

FOREIGN PATENT DOCUMENTS

| WO | 98/44134 | 10/1998 |
| WO | 99/25869 | 5/1999 |

OTHER PUBLICATIONS van Die, I, et al. "Type 1C fimbriae of a uropathogenic *Escherichia coli* strain: cloning and characterization of the genes involved in the expression of the 1C antigen and nucleotide sequence of the subunit gene", GENE, vol. 34, 1984, pp. 187–196, XP002097256.

Sekizaki, T, et al. "DNA sequence type 1 fimbrin, fpull, gene from a chicken pathogenic *Escherichia coli* serotype 078", Journal of Veterinary Medical Science, vol. 55, 1993, pp. 395–400, XP002097257.

Kruis, W et al.; "Use of probiotic substances in human medicine—current clinical studies with the apathogenic *Escherichia coli* strain Nissle 1917", Medizinishce Welt, vol. 47, No. 6, 1996, pp. A53–A57, XP002097258.

Blum et al.; "Properties of *Escherichia coli* strains of serotype 06", Plasmid, vol. 23, No. 4, Jul. 1995, pp. 234–236, XP002085750.

Georg, K. J. et al.; "Probiotische Therapie einer pseudomembranosen Kolitis. Kombination aus intestinaler Lavage und oraler Gabe von *Escherichia coli*", Deutsche Medizinische Wochenschrift, vol. 123, No. 43, 1998,pp. 1274–1278, XP002097259.

Chemical Abstracts, 3–Biochemical Genetics, vol. 128, No. 22, 1998, p. 160.

Chemical Abstracts 10–Microbial, Algal, and Fungal Biochemistry vol. 127, No. 6, 1997, p. 78305.

3–Biobhem Genetics, vol. 119, 1993, p. 218659.

Chemical Abstracts, vol. 108, 1988, p. 152.

Chemical Abstracts, vol. 103, 1985, p.138.

3–Biochem. Genetics, vol. 103, 1985, p. 65874.

3–Biochem. Genetics, vol. 101, 1984, p. 205080.

*Primary Examiner*—W. Gary Jones
*Assistant Examiner*—Janell E. Taylor
(74) *Attorney, Agent, or Firm*—Lerner, David, Littenberg, Krumholz & Mentlik, LLP

(57) ABSTRACT

The invention relates to DNA sequences from fimbrial gene clusters of *Escherichia coli* strain DSM 6601. This strain has two chromosomal fimbrial gene clusters, namely type I (fim) and FIC (foc) gene clusters. DNA sequences of the main subunits fimA and focA are represented by SEQ ID NOS: 1 and 2.

8 Claims, 2 Drawing Sheets

FIG. 1

```
DSM                                  1..........................................ATGA 4
6601 (SEQ ID NO:1)                                                               ||||
HB101 (SEQ ID NO:4)  551 GACTGCCCATGTCGATTTAGAAATAGTTTTTTGAAAGGAAAGCAGCATGA 600

5 AAATTAAAACTCTGGCAATCGTTGCTCTGTCGGCTCTGTCCCTCAGTTCC 54
                         |||||||||||||||||||||||| ||||||||||||||||||||||||
                     601 AAATTAAAACTCTGGCAATCGTTGTTCTGTCGGCTCTGTCCCTCAGTTCT 650

55 GCAGCGGCTCTGGCCG[ATACTACGACGGTAAATGGT]GGGGCCGTTCACTT 104
                         ||||||||||||||||    ||||||||  ||||||  ||| ||||||||||
                     651 ACAGCGGCTCTGGCCG CTGCCACGACGGTTAATGG GGGACCGTTCACTT 700

105 TAAAGGGGAAGTTGTTAACGCCGCTTGCGCAGTTGATGCAGGCTCTGTTG 154
                         ||||||||||||||||||||||||||||||||||||||||||||||||||
                     701 TAAAGGGGAAGTTGTTAACGCCGCTTGCGCAGTTGATGCAGGCTCTGTTG 750

155 ATCAAACCGTTCAGTTAGGCCAGGTTCGTACCGCTAGCCTGAAGCAGGAA 204
                         |||||||||||||||||||| |||||||||||||  |||   ||||||
                     751 ATCAAACCGTTCAGTTAGGACAGGTTCGTACCGCATCGCTGGCACAGGAA 800

205 GGAGCAACCAGCTCTGCCGTTGGTTTTAACATTCAGGTGAATGATTGCGA 254
                         |||||||||| ||||| || |||||||||||||||| |||||||||||||
                     801 GGAGCAACCAGTTCTGCTGTCGGTTTTAACATTCAGCTGAATGATTGCGA 850

255 TACCACTGTTGCCACAAAAGCTGCTGTTGCCTTCTTAGGTACGGCAATTG 304
                         ||||| |||||| | ||||| |||||||||||||| ||||||||| |||
                     851 TACCAATGTTGCATCTAAAGCCGCTGTTGCCTTTTTAGGTACGGCGATTG 900

305[ATGCTACCGATACTGATGTA]CTGGCTCTGCAGAGTTCAGCTGCGGGTAGC 354
                         ||||   ||||  || |  ||||||||||||||||||||||||||||||
                     901 ATGCGGGTCATACCAACGTT CTGGCTCTGCAGAGTTCAGCTGCGGGTAGC 950

355 GCAACAAACGTTGGTGTGCAGATCCTGGACAGAACGGGTGCTGCGCTGGC 404
                         |||||||||||||||||||||||||||||||||||||||||||||||| |
                     951 GCAACAAACGTTGGTGTGCAGATCCTGGACAGAACGGGTGCTGCGCTGAC 1000

405 GCTGGACGGTGCGACATTTAGTTCAGAAACAACCCTGAATAACGGAACCA 454
                         |||||| |||||||||||||||||||||||||||||||||||||||||||
                    1001 GCTGGATGGTGCGACATTTAGTTCAGAAACAACCCTGAATAACGGAACCA 1050

455 ACACCATTCCGTTCCAGGCGCGTTATTTTGCAACCGGTGCCGCAACCCCG 504
                         | |||||||||||||||||||||||||||    |||| ||||||||||||
                    1051 ATACCATTCCGTTCCAGGCGCGTTATTTTG...CCGGGGCCGCAACCCCG 1097

505 GGTGCTGCTAATGCGGATGCGACCTTCAAGGTTCAGTATCAATAA..... 549
                         ||||||||||||||||||||||||||||||||||||||||||||||
                    1098 GGTGCTGCTAATGCGGATGCGACCTTCAAGGTTCAGTATCAATAACCTAC 1157
```

FIG. 2

```
DSM             1 atgaagttaaaaattcatctccatggctgtattttcagctctgaccctggg 50
6601 (SEQ ID NO:2) ||||||||||||||||||||||||||||||||||||||||||||||||||
AD 110 (SEQ ID NO:3) 1 atgaagttaaaaattcatctccatggctgtattttcagctctgaccctggg 50

51 tgttgcgacaaatgcgtctgctgtca[ccacggttaggtgtggtacag]ttc 100
                 |||||||||||||||||||||||||| ||||||||| |||||||| |||
              51 tgttgcgacaaatgcgtctgctgtca ccacggttaatggtggtacag ttc 100

101 attttaagggtgaagtggttaatgctgcatgtgctgtaaacactaactca 150
                 ||||||||||||||||||||||||||||||||||||||||||||||||||
             101 attttaagggtgaagtggttaatgctgcatgtgctgtaaacactaactca 150

151 ttcgatcagacggttaatcttggacaggttcgttccgaaagattgaaagt 200
                 ||||||||||||||||||||||||||||||||||||||||||||||||||
             151 ttcgatcagacggttaatcttggacaggttcgttccgaaagattgaaagt 200

201 agatggagctaaaagcaatccagttggatttacaattgaattaaatgatt 250
                 ||||||||||||||||||||||||||||||||||||||||||||||||||
             201 agatggagctaaaagcaatccagttggatttacaattgaattaaatgatt 250

251 gtgactcgcaggtgtctgctggtgcaggaattgtcttttcaggcccagca 300
                 ||||||||||||||||||||||||||||||||||||||||||||||||||
             251 gtgactcgcaggtgtctgctggtgcaggaattgtcttttcaggcccagca 300

301 gttactggtaaaacagatgttcttgctttacaaagttctgcagcgggttc 350
                 ||||||||||||||||||||||||||||||||||||||||||||||||||
             301 gttactggtaaaacagatgttcttgctttacaaagttctgcagcgggttc 350

351 tgcaacaaacttcggcgttcagattactgaccataggccgaaggttgtac 400
                 ||||||||||||||||||||||||||||||||||||||||||||||||||
             351 tgcaacaaacttcggcgttcagattactgaccataggccgaaggttgtac 400

401 ctttagatggaactgcaagctcaacgtttacattaactgacggaaccaac 450
                 ||||||||||||||||||||||||||||||||||||||||||||||||||
             401 ctttagatggaactgcaagctcaacgtttacattaactgacggaaccaac 450

451 aaaattccatttcaggcggtttactacgcaactggacaggccactgc[tgg500
                 ||||||||||||||||||||||||||||||||||||||||||||||  |||
             451 aaaattccatttcaggcggtttactacgcaactggacaggccactgc tgg500

501 tattgccaacgccgacg]ccacctttaaagttcagtaccagtaa 543
                 |||||||||||||||||| ||||||||||||||||||||||||||
             501 tattgccaacgccgacg ccacctttaaagttcagtaccagtaa 543
```

DNA SEQUENCES OF GENES FROM FIMBRIAE D'ESCHERICHIA COLI STRAIN DSM 6601

The invention relates to DNA sequences from fimbrial gene clusters of *Escherichia coli* strain DSM 6601.

*Escherichia coli* is a gram-negative bacterium that occurs in human and animal intestinal flora as well as outside the intestines. *E. coli* exists in numerous varieties, which differ as regards capsule antigens, surface antigens and flagella antigens and can therefore be subdivided into numerous serological types. Classification by serotypes, however, does not provide any indication of the different virulence of the microorganisms. Representatives of one and the same serotype can have different pathogenic potential both in the human and in the animal body, ranging in the extreme case from avirulent to highly pathogenic. The *E. coli* strain DSM 6601 belongs to serogroup O6:K5, and is rated as nonpathogenic to humans or animals.

This strain has two chromosomally encoded fimbrial gene clusters, namely type I (fim) and F1C (foc) gene clusters. It is known that the fimbriae of this strain carry an adhesin. Adhesins are structures that perform an important function in the adhesion of the bacterial organism to other cells.

The main application of fimbrial genes is in analysis and diagnostics. Nevertheless, other possible applications exist in medicine and nutritional physiology and in biotechnology.

Fimbrial genes or their main subunits can be used, for example, to characterize a given strain, and so further studies of the sequence of these genes is needed.

According to the invention, studies have now been performed with *E. coli* strain DSM 6601, and the obtained DNA sequences of the main subunits fimA (FIG. 1) (SEQ ID NO:1) and focA (FIG. 2) (SEQ ID NO:2) of the fimbriae have been precisely analyzed. The DNA sequences obtained from the strain were subjected to DNA sequence analysis by means of database programs and were compared with the DNA sequences of known strains. Whereas differences compared with the strain AD 110 (SEQ ID NO:3) were found at one location of the DNA sequence in the main subunits focA of strain DSM 6601, differences relative to the comparison strain HB 101 (SEQ ID NO:4) were found at several locations in the DNA sequence of the fimA gene of strain DSM 6601, as FIGS. 1 and 2 show:

For analysis of the two main subunits fimA and focA of the fimbriae of strain DSM 6601—and of the comparison strains AD 110 and HB 101—the corresponding DNA fragments were first amplified from the chromosome of the strains by means of PCR reactions.

The invention will now be explained in more detail by means of examples:

EXAMPLES 1

Amplification of the fimA Gene From Strains DSM 6601 and HB 101

The following primer pairs were used for this PCR reaction:

fimA1: 5'-GTG TAC AGA ACG ACT GCC-3' (SEQ ID NO:5)

fimA2: 5'-GTA ATG ACG TCC CTG AAC-3' (SEQ ID NO:6)

PCR conditions:
step 1: denature for 3 min at 95° C.
step 2: 45 sec at 95° C.
step 3: 45 sec at 53° C.
step 4: 45 sec at 72° C.
step 5: 5 min at 72° C.
Steps 2 to 4 were repeated 30 times.

EXAMPLES 2

Amplification of the focA Gene From Strains DSM 6601 and AD 110

The following primer pairs were used for this PCR reaction:

focA1: 5'-CTC ACA TTG CAT TTA TGA AG-3' (SEQ ID NO:7)

focA2: 5'-GCT ATA TAT CCG TTA CAC TG-3' (SEQ ID NO:8)

PCR conditions:
step 1: denature for 3 min at 95° C.
step 2: 45 sec at 95° C.
step 3: 45 sec at 51° C.
step 4: 45 sec at 72° C.
step 5: 5 min at 72° C.
Steps 2 to 4 were repeated 30 times.

EXAMPLE 3"

Cloning and Plasmid Isolation

The PCR products obtained in Examples 1 and 2 were cloned in vector pUC 18 by the procedure of Sambrook et al. (Sambrook, J., Fritsch, E. F. and Maniatis, T., *Molecular Cloning: A laboratory manual*, Cold Spring Harbor Laboratory, second edition (1989), Cloning, Transformation: 1.53–1.84; PCR: 14.00–14.35), and the resulting plasmid DNA was transformed into the *E. coli* K12 strain DH5α.

The plasmid DNA was isolated by the procedure or Birnboim et al. (Birnboim, A. C. and Doly, J. (1979) Nucl. Acids Res. 7:1513–1523. A rapid alkaline extraction procedure for screening recombinant plasmid DNA).

3 ml of LB medium was inoculated with a bacteria colony and shaken overnight at 37° C. This culture was centrifuged in an Eppendorf tube, and the residue of medium was removed with a pipette. The cell sediment was resuspended with 100 μl of solution I (50 mM glucose; 10 mM EDTA, pH 8; 25 mM Tris-HCl, pH 8). After 5 minutes of incubation at room temperature, there was added thereto 200 μl of solution II (0.2 N NaOH; 1% SDS) and mixing was continued until the contents became clear, after which the Eppendorf tube was allowed to stand for a further 5 minutes on ice. Thereafter there was added 150 μl of solution III (3 M Na acetate, pH 4.8), shaking was performed briefly until precipitation of the chromosomal DNA in flocculent form, and the mixture was left on ice for another 5 minutes. The precipitated chromosomal DNA and the cell residues were pelleted for 5 minutes in the centrifuge, and the supernatant containing the plasmid DNA was transferred into a new tube. For purification of the plasmid DNA there were added 50 μl of phenol and 150 μl of chloroform/isoamyl alcohol (24:1), after which the contents were shaken briefly and centrifuged for 2 minutes. The aqueous phase was pipetted into a new tube. The plasmid DNA was precipitated with 2 volumes of ice-cold ethanol and centrifuged for 10 minutes. The pellet was washed with 70% ethanol and dried in the Speedvac. The plasmid DNA was resuspended in 20 μl of doubly distilled water and stored at –20° C.

EXAMPLE 4

DNA Sequencing

DNA sequencing was performed by the procedure of Sanger et al. (Sanger, F., Nicklen, S. and Coulson, A. R. (1977) Proc. Natl. Acad. Sci. USA 74: 5463–5467. DNA sequencing with chain-terminating inhibitors).

DNA sequencing was performed with the T7 sequencing kit of the Pharmacia-LKB Co.

For the denaturing step, 8 µl (1.5 to 2 µg) of plasmid DNA was mixed with 2 µl of 2 N NaOH, briefly centrifuged and incubated for 10 minutes at room temperature. The DNA was precipitated for 15 minutes at −70° C. with 3 µl of 3 M Na acetate, pH 4.8 as well as 7 µl of doubly distilled water and 60 µl of ice-cold absolute ethanol. The precipitated DNA was centrifuged for 10 minutes, washed with 70% ethanol and dried.

For the annealing reaction, the denatured DNA was suspended in 10 µl of doubly distilled water and mixed with 2 µl of annealing buffer and 2 µl (40 ng) of primer. The mixture was incubated for 20 minutes at 37° C., to allow the primer to bind to the template DNA. The reaction mixture was cooled for 10 minutes at room temperature and then either used immediately for the labeling reaction or frozen at −20° C. For the labeling reaction, 3 µl of labeling mix, 1 µl of [α-$^{32}$P]dATP and 2 µl of T7 polymerase (diluted in 1:5 ratio with enzyme dilution buffer) were pipetted into the annealing reaction mixture and, after brief mixing, were incubated for 5 minutes at room temperature. Meanwhile the sequencing mixes (2.5 µl each of 'G', 'A', 'T' and 'C' mix "short" per tube) already prepared for the termination reaction were preheated to 37° C. After completion of the labeling reaction, 4 µl aliquots thereof were added to each of the four sequencing mixes and mixed briefly with the pipette. The termination reactions were incubated for 5 minutes at 37° C. To end the termination reactions, 5 µl of stop solution were added in each case. The mixtures were then transferred into an incubator at 95° C., denatured for 2 minutes and then placed on ice. 2.5 µl aliquots of the reactions were placed on a sequencing gel [25.2 g of urea, 22 ml of doubly distilled water, 6 ml of 10×TBE, 10 ml of polyacrylamide (40%), 2 ml of ammonium persulfate (16 mg/ml) and 60 µl of TEMED), in the succession 'G', 'A', 'T', 'C'. The electrophoresis was performed at 40 watt and 1500 volt for 4.5 hours.

These DNA sequences can also be prepared synthetically in ways known in themselves, and particular sequence segments can be used as primer, in which case identification of *E. coli* strain DSM 6601 then becomes possible without difficulty. Of course, the possibility also exists that the corresponding DNA sequences of this strain can be introduced by genetic engineering into other *E. coli* strains, in order, for example, to modify the behavior as regards adhesion of the cells and thus to influence the colonization properties of other strains.

SEQUENCE PROTOCOL

GENERAL INFORMATION

| | |
|---|---|
| APPLICANT: | PHARMA-ZENTRALE GMBH |
| | LOERFELDSTRASSE 20 |
| | 58313 HERDECKE |
| | FEDERAL REPUBLIC OF |
| | GERMANY |
| TITLE OF THE INVENTION: | DNA SEQUENCES FROM |
| | FIMBRIAL GENES OF |
| | *ESCHERICHIA COLI* |
| | STRAIN DSM 6601 |
| NUMBER OF SEQUENCES: | 2 |
| COMPUTER-READABLE VERSION: | |
| DATA MEDIUM | DISKETTE |
| COMPUTER | IBM COMPATIBLE |
| OPERATING SYSTEM | WINDOWS 95 |
| SOFTWARE | MICROSOFT WORD 6.0 |

DATA OF THE PRESENT APPLICATION

APPLICATION NUMBER
APPLICATION DATE
AGENT INFORMATION

| | |
|---|---|
| NAME | DRES. HARMSEN & |
| | UTESCHER |
| AGENT NUMBER | 268569 |
| FILE NUMBER | PT 19/97 |
| TEL | 040-249757 |
| FAX | 040-2803672 |
| SEQUENCE ID NO. INFORMATION: | fimadsm |

SEQUENCE CHARACTERISTICS:

| | |
|---|---|
| LENGTH | 549 BASE PAIRS |
| TYPE | DNA |
| STRAND FORM | DOUBLE STRAND |
| TOPOLOGY | LINEAR |

ORIGINAL SOURCE:

| | |
|---|---|
| ORGANISM | *ESCHERICHIA COLI* |
| STRAIN | DSM 6601 |
| CELL TYPE | SINGLE-CELLED ORGANISM |

BIBLIOGRAPHY:

| | |
|---|---|
| AUTHORS | KLEMM, P. |
| TITLE | The fimA gene encoding the type 1 fimbrial subunit of *Escherichia coli* |
| PERIODICAL | EUR. J., BIOCHEM. |
| VOLUME | 143 (2) |
| PAGES | 395–399 |
| DATE | 1984 |

```
SEQUENCE DESCRIPTION                    SEQ ID NO: fimadsm

1 ATGAAAATTA AAACTCTGGC AATCGTTGCT CTGTCGGCTC TGTCCCTCAG

51 TTCCGCAGCG GCTCTGGCCG ATACTACGAC GGTAAATGGT GGGGCCGTTC

101 ACTTTAAAGG GGAAGTTGTT AACGCCGCTT GCGCAGTTGA TGCAGGCTCT

151 GTTGATCAAA CCGTTCAGTT AGGCCAGGTT CGTACCGCTA GCCTGAAGCA

201 GGAAGGAGCA ACCAGCTCTG CCGTTGGTTT TAACATTCAG GTGAATGATT

251 GCGATACCAC TGTTGCCACA AAAGCTGCTG TTGCCTTCTT AGGTACGGCA

301 ATTGATGCTA CCGATACTGA TGTACTGGCT CTGCAGAGTT CAGCTGCGGG

351 TAGCGCAACA AACGTTGGTG TGCAGATCCT GGACAGAACG GGTGCTGCGC

401 TGACGCTGGA CGGTGCGACA TTTAGTTCAG AAACAACCCT GAATAACGGA

451 ACCAATACCA TTCCGTTCCA GGCGCGTTAT TTTGCAACCG GTGCCGCAAC

501 CCCGGGTGCT GCTAATGCGG ATGCGACCTT CAAGGTTCAG TATCAATAA
```

SEQUENCE PROTOCOL

GENERAL INFORMATION

| | |
|---|---|
| APPLICANT: | PHARMA-ZENTRALE GMBH<br>LOERFELDSTRASSE 20<br>58313 HERDECKE<br>FEDERAL REPUBLIC OF<br>GERMANY |
| TITLE OF THE INVENTION: | DNA SEQUENCES FROM<br>FIMBRIAL GENES OF<br>*ESCHERICHIA COLI*<br>STRAIN DSM 6601 |
| NUMBER OF SEQUENCES: | 2 |
| COMPUTER-READABLE VERSION: | |
| DATA MEDIUM | DISKETTE |
| COMPUTER | IBM COMPATIBLE |
| OPERATING SYSTEM | WINDOWS 95 |
| SOFTWARE | MICROSOFT WORD 6.0 |
| DATA OF THE PRESENT APPLICATION | |
| APPLICATION NUMBER | |
| APPLICATION DATE | |

SEQUENCE PROTOCOL

AGENT INFORMATION

| | |
|---|---|
| NAME | DRES. HARMSEN &<br>UTESCHER |
| AGENT NUMBER | 268569 |
| FILE NUMBER | PT 19/97 |
| TEL | 040-249757 |
| FAX | 040-2803672 |
| SEQUENCE ID NO. INFORMATION: | focadsm |
| SEQUENCE CHARACTERISTICS: | |
| LENGTH | 543 BASE PAIRS |
| TYPE | DNA |
| STRAND FORM | DOUBLE STRAND |
| TOPOLOGY | LINEAR |
| ORIGINAL SOURCE: | |
| ORGANISM | *ESCHERICHIA COLI* |
| STRAIN | DSM 6601 |
| CELL TYPE | SINGLE-CELLED ORGANISM |
| SEQUENCE DESCRIPTION | SEQ ID NO: focadsm |

```
SEQUENCE DESCRIPTION                    SEQ ID NO: focadsm 1 atgaagttaa aatccatctc catggctgta ttttcagctc tgtccctggg 51 tgttgcgaca aatgcgtctg ctgtcaccac ggttaggtgt ggtacagttc 101 attttaaggg tgaagtggtt aatgctgcat gtgctgtaaa cactaactca 151 ttcgatcaga cggttaatct tggacaggtt cgttccgaaa gattgaaagt 201 agatggagct aaaagcaatc cagttggatt tacaattgaa ttaaatgatt 251 gtgactcgca ggtgtctgct ggtgcaggaa ttgtcttttc aggcccagca 301 gttactggta aaacagatgt tcttgcttta caaagttctg cagcgggttc 351 tgcaacaaac ttcggcgttc agattactga ccataggccg aaggttgtac 401 ctttagatgg aactgcaagc tcaacgttta cattaactga cggaaccaac 451 aaaattccat ttcaggcggt ttactacgca actggacagg ccactgctgg 501 tattgccaac gccgacgcca cctttaaagt tcagtaccag taa
```

What is claimed is:

1. A nucleic acid having the nucleotide sequence designated SEQ. ID NO. 1.

2. A reagent comprising a nucleic acid of claim 1.

3. A nucleic acid amplification kit comprising a nucleic acid of claim 1.

4. A recombinant *Escherichia coli* containing a nucleic acid of claim 1.

5. A nucleic acid having the nucleotide sequence designated SEQ. ID NO. 2.

6. A reagent comprising a nucleic acid of claim 5.

7. A nucleic acid amplification kit comprising a nucleic acid of claim 5.

8. A recombinant *Escherichia coli* containing a nucleic acid of claim 5.

* * * * *

SEQUENCE LISTING

<160> NUMBER OF SEQ ID NOS: 8

<210> SEQ ID NO 1
<211> LENGTH: 549
<212> TYPE: DNA
<213> ORGANISM: Escherichia coli

<400> SEQUENCE: 1

| | | | | | |
|---|---|---|---|---|---|
| atgaaaatta | aaactctggc | aatcgttgct | ctgtcggctc | tgtccctcag | ttccgcagcg | 60 |
| gctctggccg | atactacgac | ggtaaatggt | ggggccgttc | actttaaagg | ggaagttgtt | 120 |
| aacgccgctt | gcgcagttga | tgcaggctct | gttgatcaaa | ccgttcagtt | aggccaggtt | 180 |
| cgtaccgcta | gcctgaagca | ggaaggagca | accagctctg | ccgttggttt | taacattcag | 240 |
| gtgaatgatt | gcgataccac | tgttgccaca | aaagctgctg | ttgccttctt | aggtacggca | 300 |
| attgatgcta | ccgatactga | tgtactggct | ctgcagagtt | cagctgcggg | tagcgcaaca | 360 |
| aacgttggtg | tgcagatcct | ggacagaacg | ggtgctgcgc | tgacgctgga | cggtgcgaca | 420 |
| tttagttcag | aaacaaccct | gaataacgga | accaatacca | ttccgttcca | ggcgcgttat | 480 |
| tttgcaaccg | gtgccgcaac | cccgggtgct | gctaatgcgg | atgcgacctt | caaggttcag | 540 |
| tatcaataa | | | | | 549 |

<210> SEQ ID NO 2
<211> LENGTH: 543
<212> TYPE: DNA
<213> ORGANISM: Escherichia coli

<400> SEQUENCE: 2

| | | | | | |
|---|---|---|---|---|---|
| atgaagttaa | aattcatctc | catggctgta | ttttcagctc | tgaccctggg | tgttgcgaca | 60 |
| aatgcgtctg | ctgtcaccac | ggttaggtgt | ggtacagttc | attttaaggg | tgaagtggtt | 120 |
| aatgctgcat | gtgctgtaaa | cactaactca | ttcgatcaga | cggttaatct | tggacaggtt | 180 |
| cgttccgaaa | gattgaaagt | agatggagct | aaaagcaatc | cagttggatt | tacaattgaa | 240 |
| ttaaatgatt | gtgactcgca | ggtgtctgct | ggtgcaggaa | ttgtcttttc | aggcccagca | 300 |
| gttactggta | aaacagatgt | tcttgcttta | caaagttctg | cagcgggttc | tgcaacaaac | 360 |
| ttcggcgttc | agattactga | ccataggccg | aaggttgtac | ctttagatgg | aactgcaagc | 420 |
| tcaacgttta | cattaactga | cggaaccaac | aaaattccat | tcaggcggt | ttactacgca | 480 |
| actggacagg | ccactgctgg | tattgccaac | gccgacgcca | cctttaaagt | tcagtaccag | 540 |
| taa | | | | | 543 |

<210> SEQ ID NO 3
<211> LENGTH: 543
<212> TYPE: DNA
<213> ORGANISM: Escherichia coli

<400> SEQUENCE: 3

| | | | | | |
|---|---|---|---|---|---|
| atgaagttaa | aattcatctc | catggctgta | ttttcagctc | tgaccctggg | tgttgcgaca | 60 |
| aatgcgtctg | ctgtcaccac | ggttaatggt | ggtacagttc | attttaaggg | tgaagtggtt | 120 |
| aatgctgcat | gtgctgtaaa | cactaactca | ttcgatcaga | cggttaatct | tggacaggtt | 180 |
| cgttccgaaa | gattgaaagt | agatggagct | aaaagcaatc | cagttggatt | tacaattgaa | 240 |
| ttaaatgatt | gtgactcgca | ggtgtctgct | ggtgcaggaa | ttgtcttttc | aggcccagca | 300 |
| gttactggta | aaacagatgt | tcttgcttta | caaagttctg | cagcgggttc | tgcaacaaac | 360 |

```
ttcggcgttc agattactga ccataggccg aaggttgtac ctttagatgg aactgcaagc      420
tcaacgttta cattaactga cggaaccaac aaaattccat ttcaggcggt ttactacgca      480
actggacagg ccactgctgg tattgccaac gccgacgcca cctttaaagt tcagtaccag      540
taa                                                                   543

<210> SEQ ID NO 4
<211> LENGTH: 597
<212> TYPE: DNA
<213> ORGANISM: Escherichia coli

<400> SEQUENCE: 4
gactgcccat gtcgatttag aaatagtttt ttgaaaggaa agcagcatga aaattaaaac       60
tctggcaatc gttgttctgt cggctctgtc cctcagttct acagcggctc tggccgctgc      120
cacgacggtt aatggtggga ccgttcactt taaaggggaa gttgttaacg ccgcttgcgc      180
agttgatgca ggctctgttg atcaaaccgt tcagttagga caggttcgta ccgcatcgct      240
ggcacaggaa ggagcaacca gttctgctgt cggttttaac attcagctga atgattgcga      300
taccaatgtt gcatctaaag ccgctgttgc cttttaggt acggcgattg atgcgggtca       360
taccaacgtt ctggctctgc agagttcagc tgcgggtagc gcaacaaacg ttggtgtgca      420
gatcctggac agaacgggtg ctgcgctgac gctggatggt gcgacattta gttcagaaac      480
aaccctgaat aacggaacca ataccattcc gttccaggcg cgttattttg ccggggccgc      540
aaccccgggt gctgctaatg cggatgcgac cttcaaggtt cagtatcaat aacctac        597

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 5
gtgtacagaa cgactgcc                                                    18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 6
gtaatgacgt ccctgaac                                                    18

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 7
ctcacattgc atttatgaag                                                  20

<210> SEQ ID NO 8
<211> LENGTH: 20
<212> TYPE: DNA
<213> ORGANISM: Artificial Sequence
<220> FEATURE:
```

-continued

<223> OTHER INFORMATION: Description of Artificial Sequence: Primer

<400> SEQUENCE: 8
gctatatatc cgttacactg                                              20